(12) United States Patent
Vraney et al.

(10) Patent No.: US 8,870,957 B2
(45) Date of Patent: Oct. 28, 2014

(54) IMPLANT FOR MAMMALIAN BONY SEGMENT STABILIZATION

(75) Inventors: Robert Tod Vraney, Evansville, IN (US); Todd Stanaford, Midland, TX (US); Leonel Dominguez, Jacksonville, FL (US)

(73) Assignee: Amendia, Inc., Marietta, GA (US)

( * ) Notice: Subject to any disclaimer, the term of this patent is extended or adjusted under 35 U.S.C. 154(b) by 230 days.

(21) Appl. No.: 12/398,111

(22) Filed: Mar. 4, 2009

(65) Prior Publication Data

US 2010/0228296 A1 Sep. 9, 2010

(51) Int. Cl.
*A61F 2/44* (2006.01)
*A61F 2/28* (2006.01)
*A61F 2/30* (2006.01)
*A61F 2/46* (2006.01)

(52) U.S. Cl.
CPC . *A61F 2/447* (2013.01); *A61F 2/28* (2013.01); *A61F 2002/2817* (2013.01); *A61F 2002/3008* (2013.01); *A61F 2002/30176* (2013.01); *A61F 2002/30785* (2013.01); *A61F 2002/30904* (2013.01); *A61F 2002/4475* (2013.01); *A61F 2002/448* (2013.01); *A61F 2002/4629* (2013.01); *A61F 2230/0054* (2013.01); *A61F 2250/0098* (2013.01); *A61F 2310/00293* (2013.01); *A61F 2310/00359* (2013.01)
USPC ........................................ 623/17.11; 606/246

(58) Field of Classification Search
USPC .................................. 606/246–249, 90, 105; 623/17.11–17.16
See application file for complete search history.

(56) References Cited

U.S. PATENT DOCUMENTS

| | | | |
|---|---|---|---|
| 5,026,373 A * | 6/1991 | Ray et al. ..................... 606/86 A |
| 5,522,899 A | 6/1996 | Michelson | |
| 5,860,973 A | 1/1999 | Michelson | |
| 5,888,227 A * | 3/1999 | Cottle ........................ 623/17.16 |
| 6,123,705 A | 9/2000 | Michelson | |
| 6,231,610 B1 | 5/2001 | Geisler | |
| 6,235,059 B1 | 5/2001 | Benezech et al. | |
| 6,500,205 B1 | 12/2002 | Michelson | |
| 6,558,423 B1 | 5/2003 | Michelson | |
| 6,558,424 B2 | 5/2003 | Thalgott | |
| 6,576,017 B2 | 6/2003 | Foley et al. | |
| 6,706,070 B1 | 3/2004 | Wagner et al. | |
| 6,723,128 B2 | 4/2004 | Uk | |
| 6,730,127 B2 | 5/2004 | Michelson | |
| 6,773,460 B2 | 8/2004 | Jackson | |
| 7,112,222 B2 | 9/2006 | Fraser et al. | |
| 7,137,997 B2 | 11/2006 | Paul | |
| 7,163,561 B2 | 1/2007 | Michelson | |
| 7,172,627 B2 | 2/2007 | Fiere et al. | |
| 7,442,209 B2 | 10/2008 | Michelson | |
| 2002/0029084 A1 | 3/2002 | Paul et al. | |
| 2002/0055745 A1 | 5/2002 | McKinley | |
| 2003/0040798 A1 * | 2/2003 | Michelson ................. 623/17.11 |
| 2005/0119753 A1 | 6/2005 | McGahan et al. | |
| 2005/0125062 A1 | 6/2005 | Biedermann et al. | |

(Continued)

FOREIGN PATENT DOCUMENTS

| | | |
|---|---|---|
| WO | 2004069106 A1 | 8/2004 |
| WO | 2007098288 A2 | 8/2007 |
| WO | 2009091775 A2 | 7/2009 |

*Primary Examiner* — Mary Hoffman
*Assistant Examiner* — Tara Carter
(74) *Attorney, Agent, or Firm* — David L King

(57) ABSTRACT

Embodiments of bony region stabilization implants including multiple fenestrations and bony ingrowth materials are described generally herein. Other embodiments may be described and claimed.

16 Claims, 11 Drawing Sheets

(56) References Cited

U.S. PATENT DOCUMENTS

| | | |
|---|---|---|
| 2005/0131536 A1 | 6/2005 | Eisermann et al. |
| 2005/0154459 A1 | 7/2005 | Wolek et al. |
| 2005/0171554 A1 | 8/2005 | Estes et al. |
| 2005/0177245 A1 | 8/2005 | Leatherbury et al. |
| 2007/0027544 A1* | 2/2007 | McCord et al. ............ 623/17.11 |
| 2008/0177307 A1 | 7/2008 | Moskowitz et al. |
| 2009/0234455 A1 | 9/2009 | Moskowitz et al. |

* cited by examiner

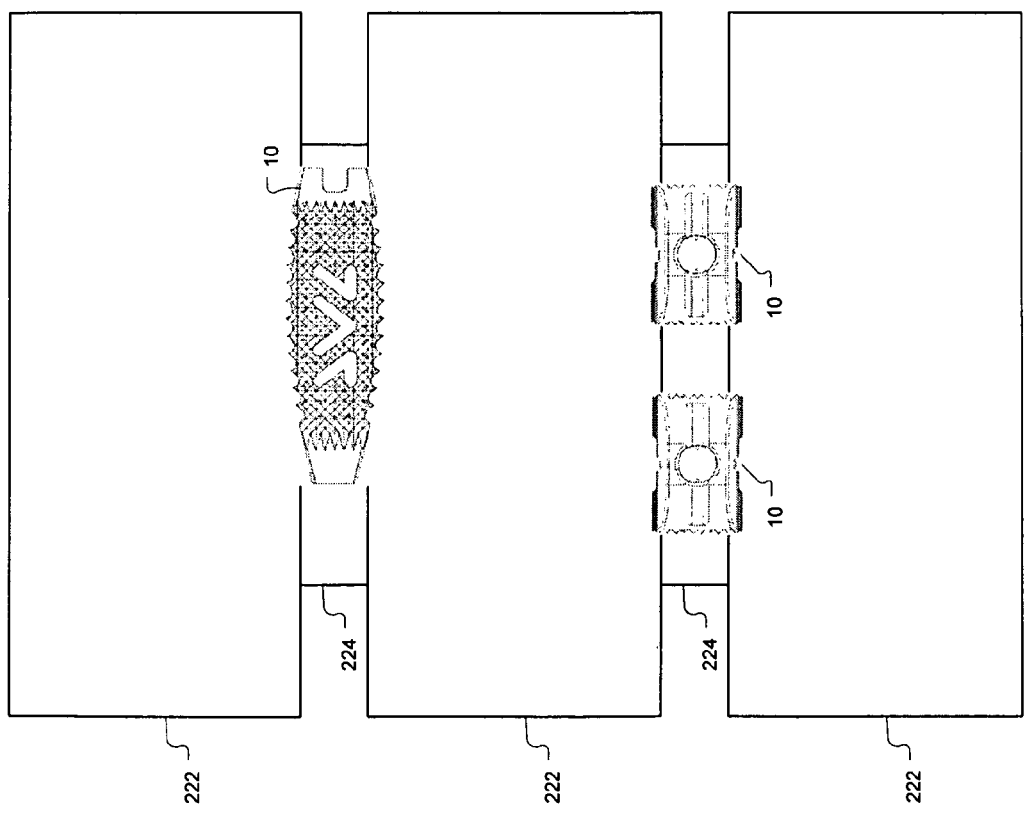

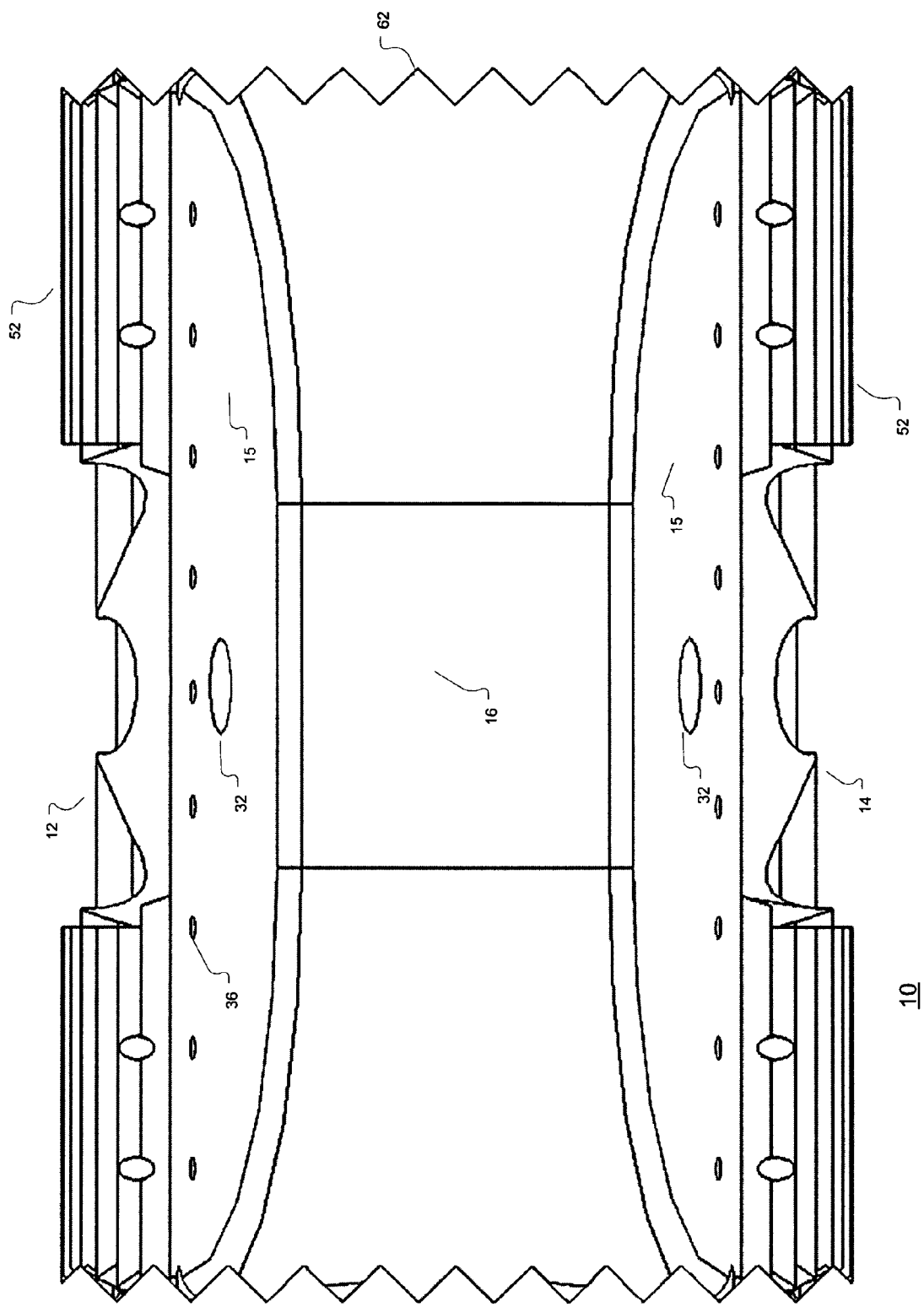

IMPLANT FOR MAMMALIAN BONY SEGMENT STABILIZATION

TECHNICAL FIELD

Various implant embodiments described herein relate generally to stabilizing mammalian bony segments, including fenestrated implants to stabilize one or more mammalian bony segments.

BACKGROUND INFORMATION

It may be desirable to stabilize one or more bony segments via one or more implants, the present invention provides such implants.

BRIEF DESCRIPTION OF THE DRAWINGS

FIG. 1 is a simplified diagram of mammalian bony segment stabilization architecture according to various embodiments.

FIG. 2H is a simplified, front view of a mammalian bony segment stabilization implant according to various embodiments.

FIG. 2I is a simplified, rear view of a mammalian bony segment stabilization implant according to various embodiments.

DETAILED DESCRIPTION

FIG. 1 is a simplified diagram of a mammalian bony segment stabilization architecture 220 according to various embodiments. The architecture 220 includes one or more implants 10 inserted between bony regions 222 at multiple levels. In an embodiment one or more implants 10 may be inserted laterally as shown between the top, two bony regions 222. In another embodiment one or more implants 10 may be inserted posteriorly as shown between the bottom, two bony regions 222. Further one or more implants 10 may be inserted laterally and one or more implants 10 may be inserted posteriorly between two bony regions 222. Additionally the implants 10 may inserted at any angle between two bony regions 222 as a function of anatomy adjacent to the two bony regions 222.

Figure 2A:
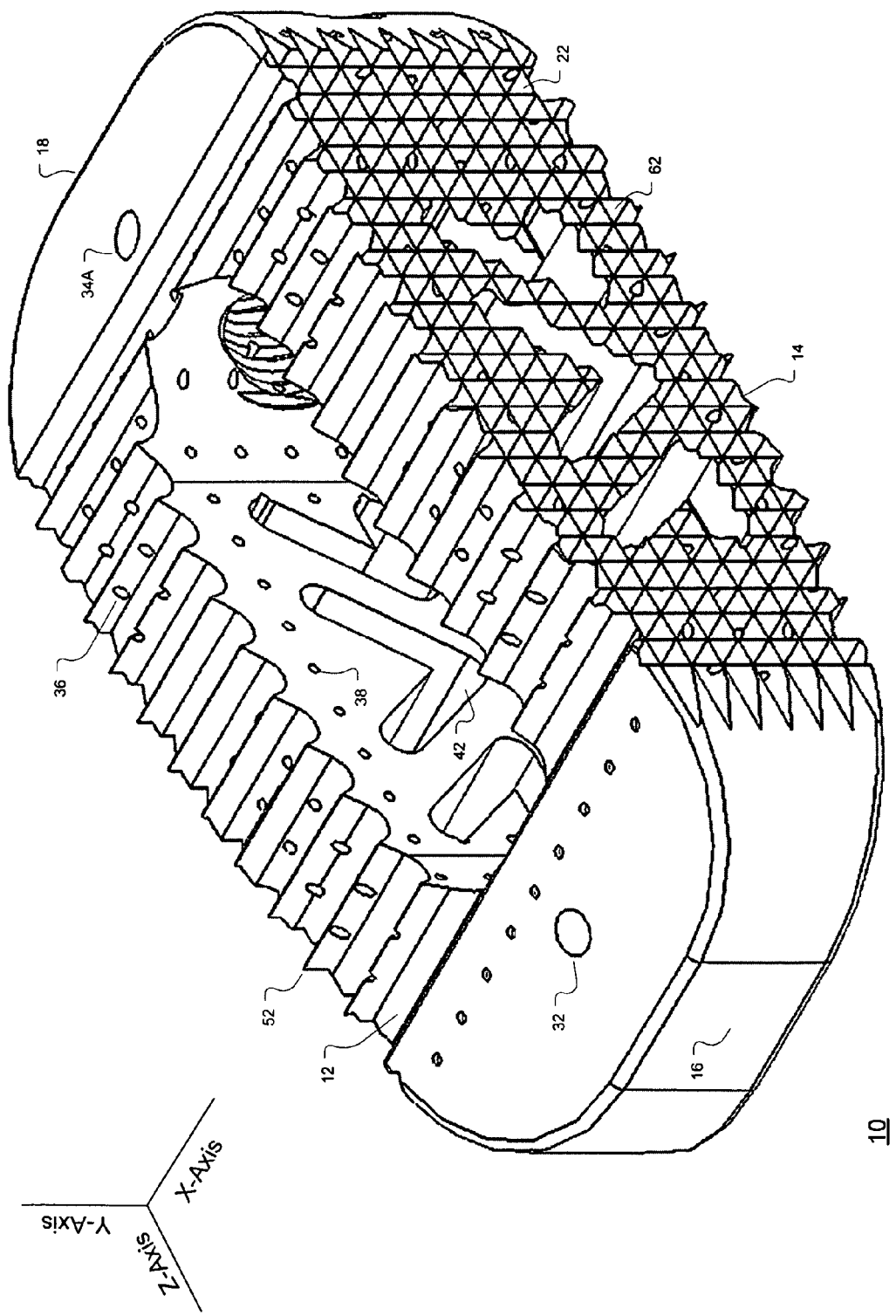
FIG. 2A is a simplified, isometric front view of a mammalian bony segment stabilization implant according to various embodiments.
Figure 2B:
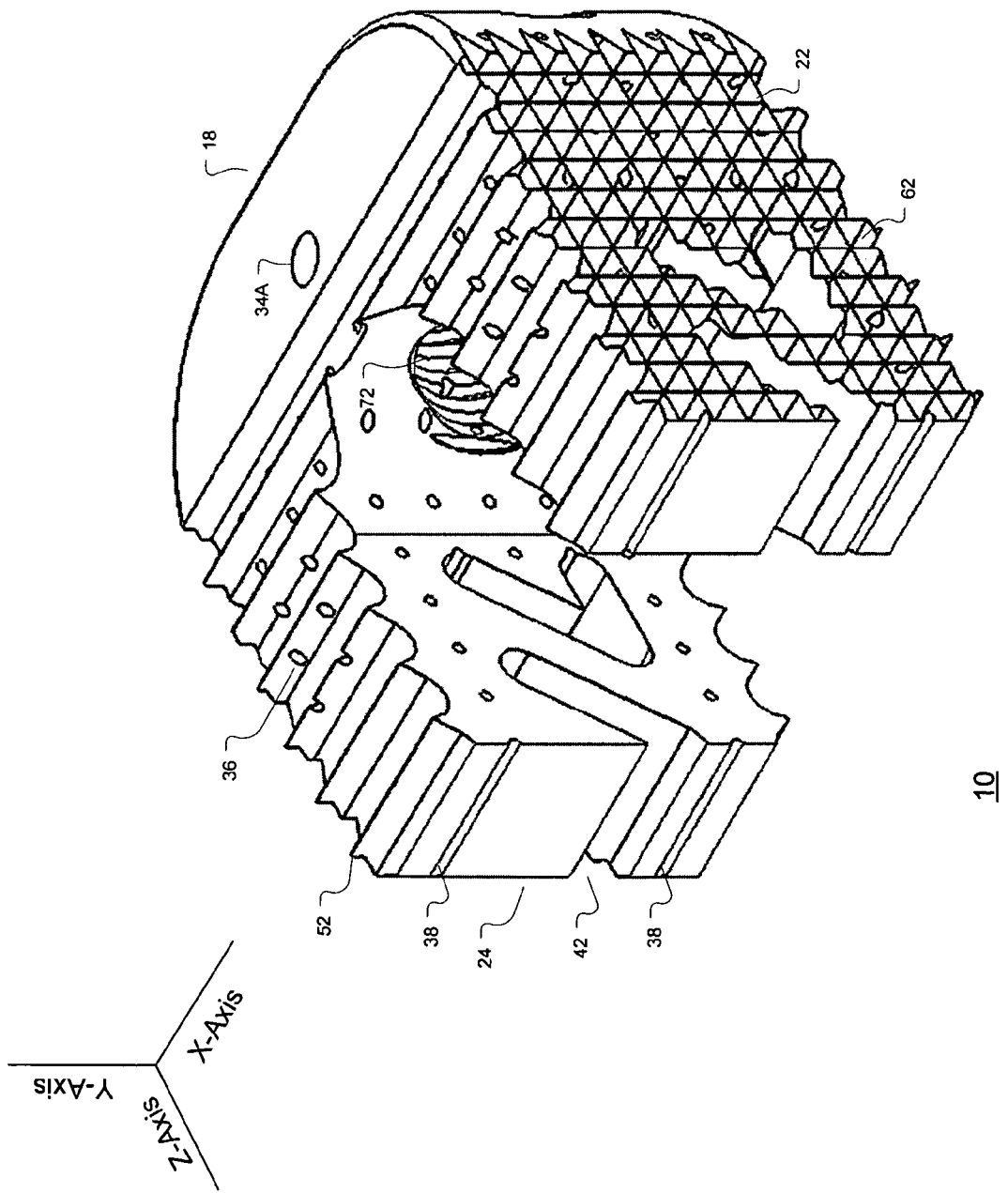
FIG. 2B is a simplified, isometric X-Y sectional front view of a mammalian bony segment stabilization implant according to various embodiments.
Figure 2C:
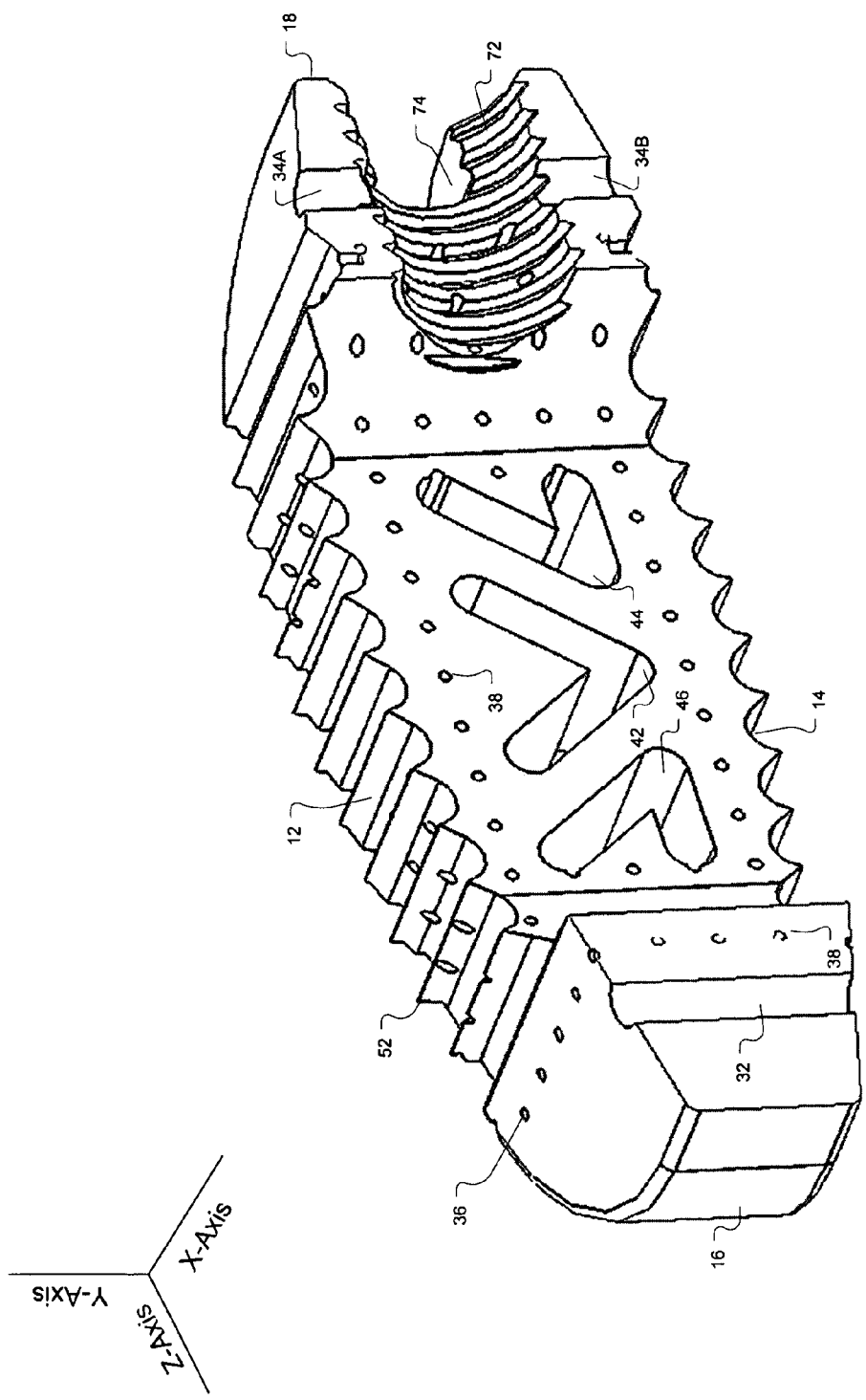
FIG. 2C is a simplified, isometric Y-Z sectional front view of a mammalian bony segment stabilization implant according to various embodiments.
Figure 2D:
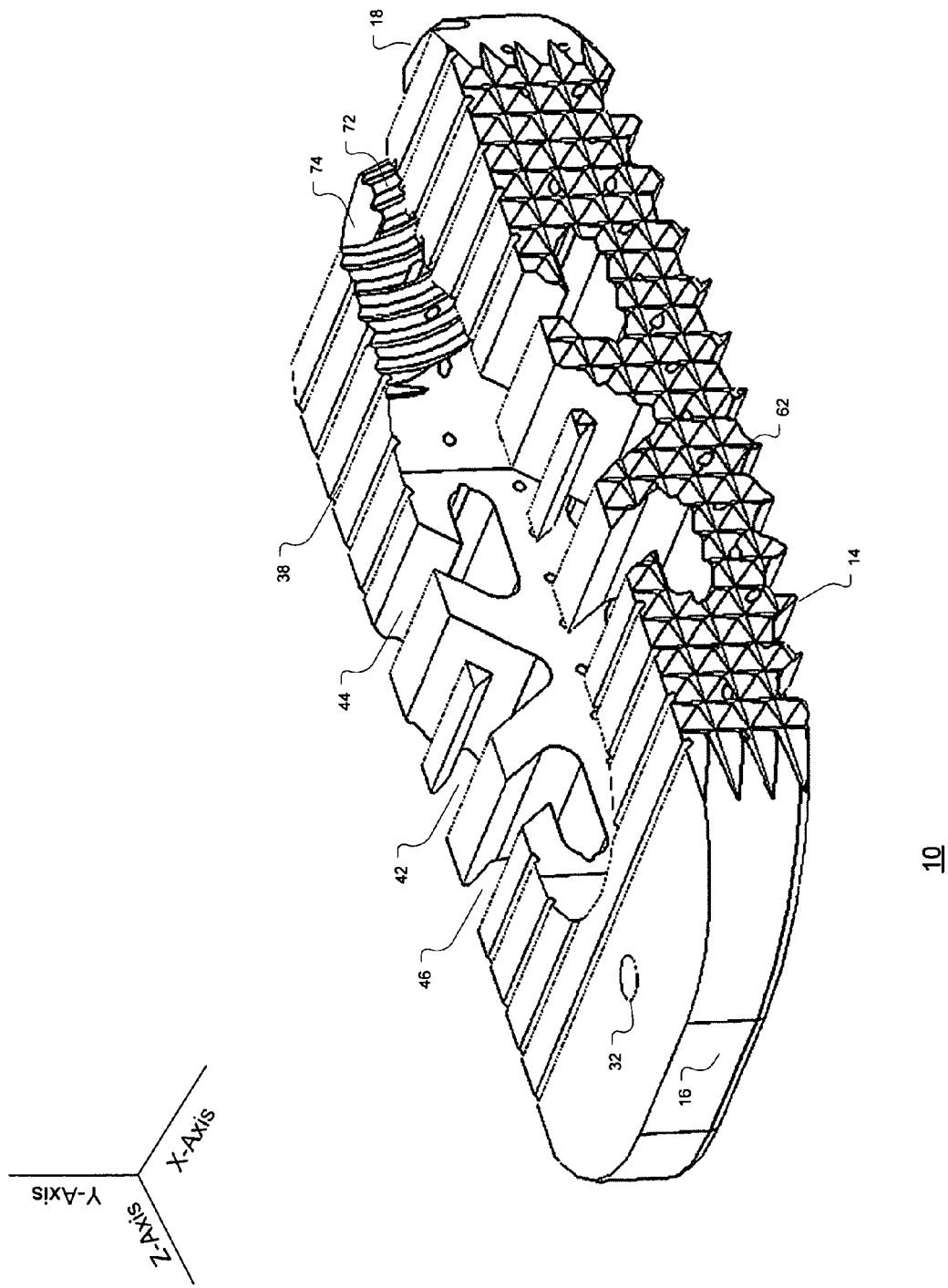
FIG. 2D is a simplified, isometric X-Z sectional front view of a mammalian bony segment stabilization implant according to various embodiments.

FIG. 2A is a simplified, isometric front view of a mammalian bony segment stabilization implant 10 according to various embodiments. In an embodiment the implant has an elongated shape including a front 16, first side 24, second side 22, rear 18, top 12, and bottom 14. The implant 10 may include a large central fenestration extending from the top surface 12 to the bottom surface 14. The implant 10 may include partial fenestrations or porous openings 36 spaced periodically along the top and bottom surfaces 12, 14. The implant 10 may further include fenestrations or porous openings 32, 34A, 34B along one or more axis where one or more radio opaque markers 84, 82A, 82B (FIG. 2K).

The implant 10 may further include partial or full lateral (along X-Axis) fenestrations or porous openings 38 in the side walls 12, 14 extending to the central fenestration or opening 37. The implant 10 may further include several larger fenestrations or openings 42, 44, 46 extending through each side wall 12, 14 to the central fenestration 37. The fenestration or opening 42 may be V-shaped and the fenestrations or openings 44, 46 may be arrow shaped in an embodiment. The implant 10 top 12 and bottom surfaces 14 may include a plurality of racked teeth 52. The implant 10 side surfaces 22, 24 may include a plurality of protrusions 62.

Figure 2E:
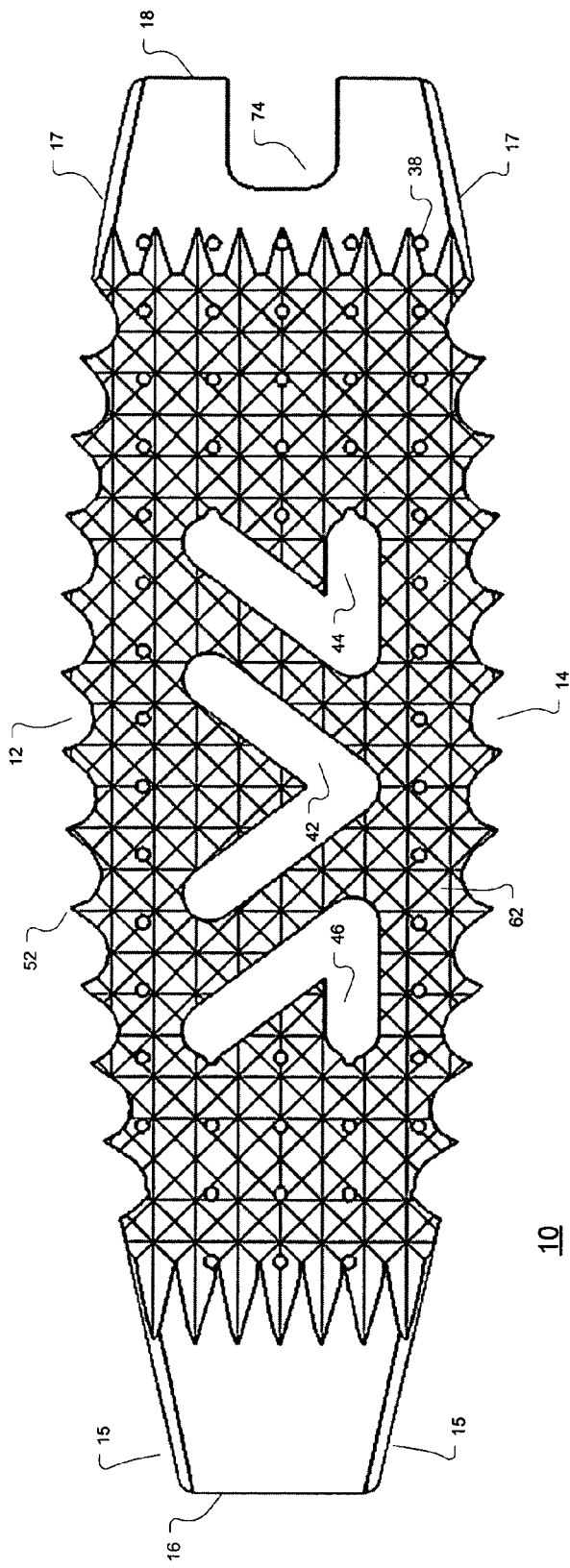
FIG. 2E is a simplified, side view of a mammalian bony segment stabilization implant according to various embodiments.

In an embodiment the implant front surface 16 may have sloped surfaces 15 coupling the front surface 16 to the top and bottom 12, 14 surfaces (FIG. 2E). In addition the implant rear surface 18 may also have sloped surfaces 17 coupling the rear surface 18 to the top and bottom 12, 14 surfaces. In an embodiment the implant 10 may be sized to be inserted between two lumbar vertebra. In an embodiment the implant's maximum height between the top surface 12 and bottom surface 14 may be about 8 mm. The implant's maximum length between the front surface 16 and rear surface 18 may be about 26 mm. In such an embodiment the fenestrations or porous openings 32, 34A, and 34B may have a diameter of about 1 mm, the fenestrations or porous openings 36, 38 may have a diameter of about 0.25 mm. The central fenestration 37 may have a maximum length of about 16 mm and a maximum width of about 5 mm. The fenestration 37 ends may a radius of about 2.5 mm.

In an embodiment the front surfaces 15 may have a slope of about 25 degrees. Further the top and bottom surfaces 12, 14 may have an effective radius of about 46 mm. The implant 10 rear surface 18 may have a tool interface 74 including a threaded section 72 (FIG. 2I). In an embodiment the depth and height of the tool opening may be 2 mm and the threaded section 72 may have a diameter about 4 mm with a total depth of about 4 mm. The fenestrations or porous openings 36 on the top 12 and bottom 14 surfaces and fenestrations 38 or openings on the sides 22, 24 may have a spacing about 1.25 mm vertically and horizontally from each adjacent fenestration.

Figure 2F:
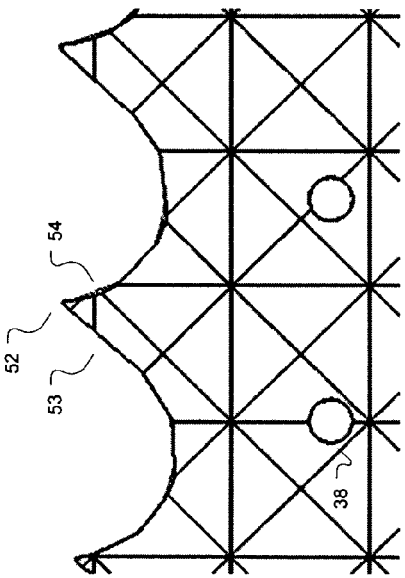
FIG. 2F is a simplified, partial view of a mammalian bony segment stabilization implant top and bottom teeth according to various embodiments.

The implant 10 top 12 and bottom 14 surfaces may have teeth (FIG. 2F). In an embodiment the teeth 52 may be spaced about 1.4 mm apart and have a height of about 0.6 mm. The teeth 52 surface 53 may have reverse rack (relative to the implant 10 front 16) of about 52 degrees (obtuse) and the surface 54 having an acute angle relative to normal.

In an embodiment the implant 10 may be include a radio lucent material including polymers/thermoplastics such as PEEK (Polyetheretherketone). The radio markers may include radio opaque materials including metal alloys such as titanium and tantalum. As noted the implant 10 includes a large central fenestration 37, side fenestrations 38, and top and bottom surface fenestrations 36. The fenestrations or porous openings 36, 37, 38 may enable bony in-growth in the implant 10. The implant 10 material may include a bone growth activator or bio-active elements including a calcium based hydroxylapatite or hydroxyapatite. The implant 10 surfaces 12, 14, 16, 18, 22, 24 and fenestration or porous opening 36, 37, 38 surfaces may be coated with a bio-active element or coatings including a hydroxyapatite to encourage bony growth between a bony surface 222 and an implant 10. The entire implant 10 may be coated with one or more bio-active elements including a hydroxyapatite.

FIG. 2B is a simplified, isometric X-Y sectional front view of the mammalian bony segment stabilization implant 10 according to various embodiments. As shown in FIG. 2B the side fenestrations 38 may extend from a side surface 22, 24 to the central fenestration 37. FIG. 2C is a simplified, isometric Y-Z sectional front view of the mammalian bony segment stabilization implant 10 according to various embodiments. As shown in FIG. 2C the fenestration 32 may extend through the implant 10 and the fenestrations 34A, 34B may extend from the top 12 and bottom 14 surfaces respectively to the tool engagement 74 thread 72.

FIG. 2D is a simplified, isometric X-Z sectional front view of the mammalian bony segment stabilization implant 10 according to various embodiments. As shown in FIG. 2D, the side fenestrations 38, 42, 44, 46 may extend from a side surface 22, 24 to the central fenestration 37. FIG. 2E is a simplified, left side view 24 of the mammalian bony segment stabilization implant 10 according to various embodiments. As shown in FIG. 2E the side surfaces 22, 24 include a diamond knurl pattern 62 on a substantial section and racked teeth 52 along the top 12 and bottom 14 surfaces.

Figure 2G:
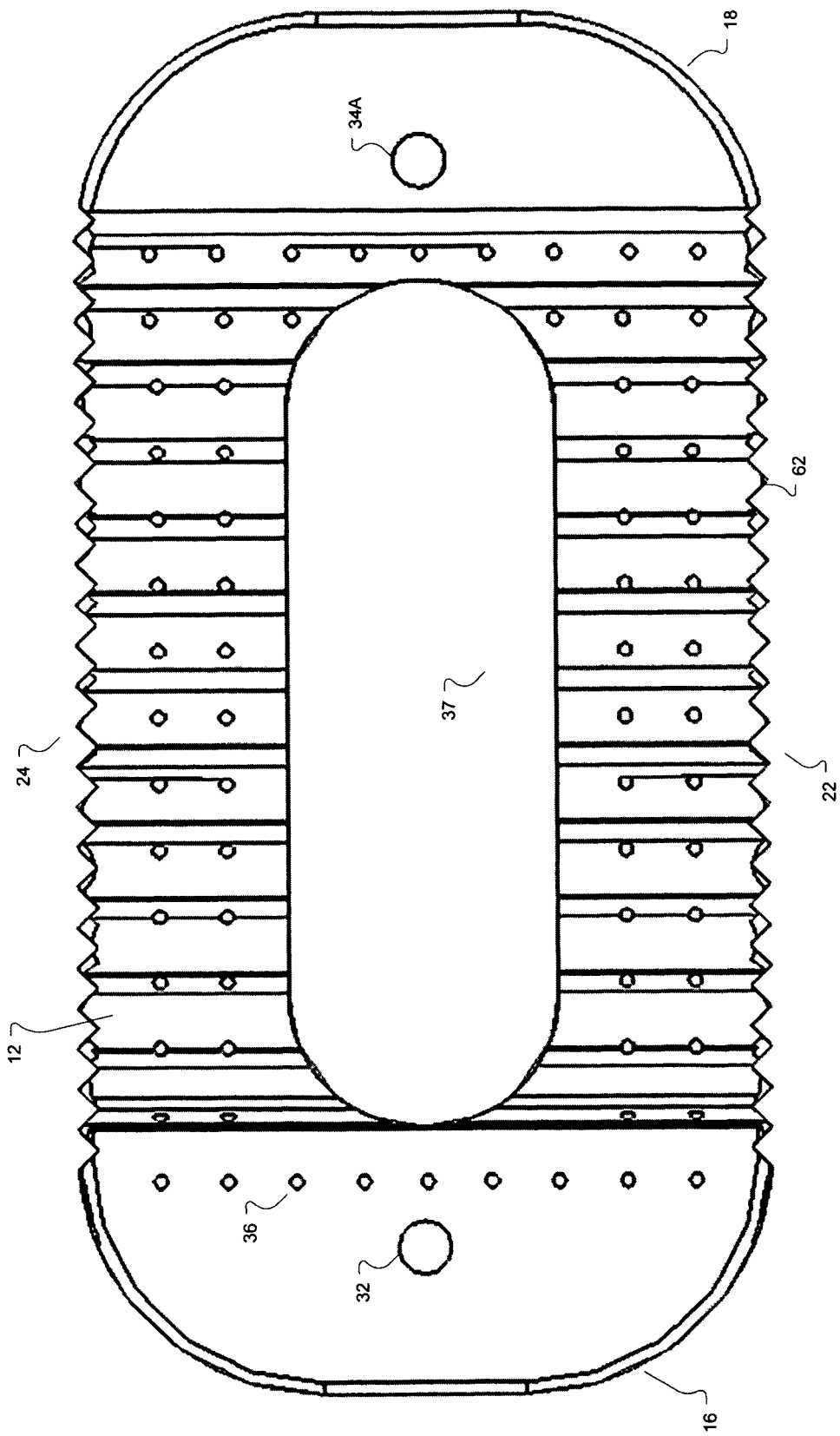
FIG. 2G is a simplified, top view of a mammalian bony segment stabilization implant according to various embodiments.
Figure 21:
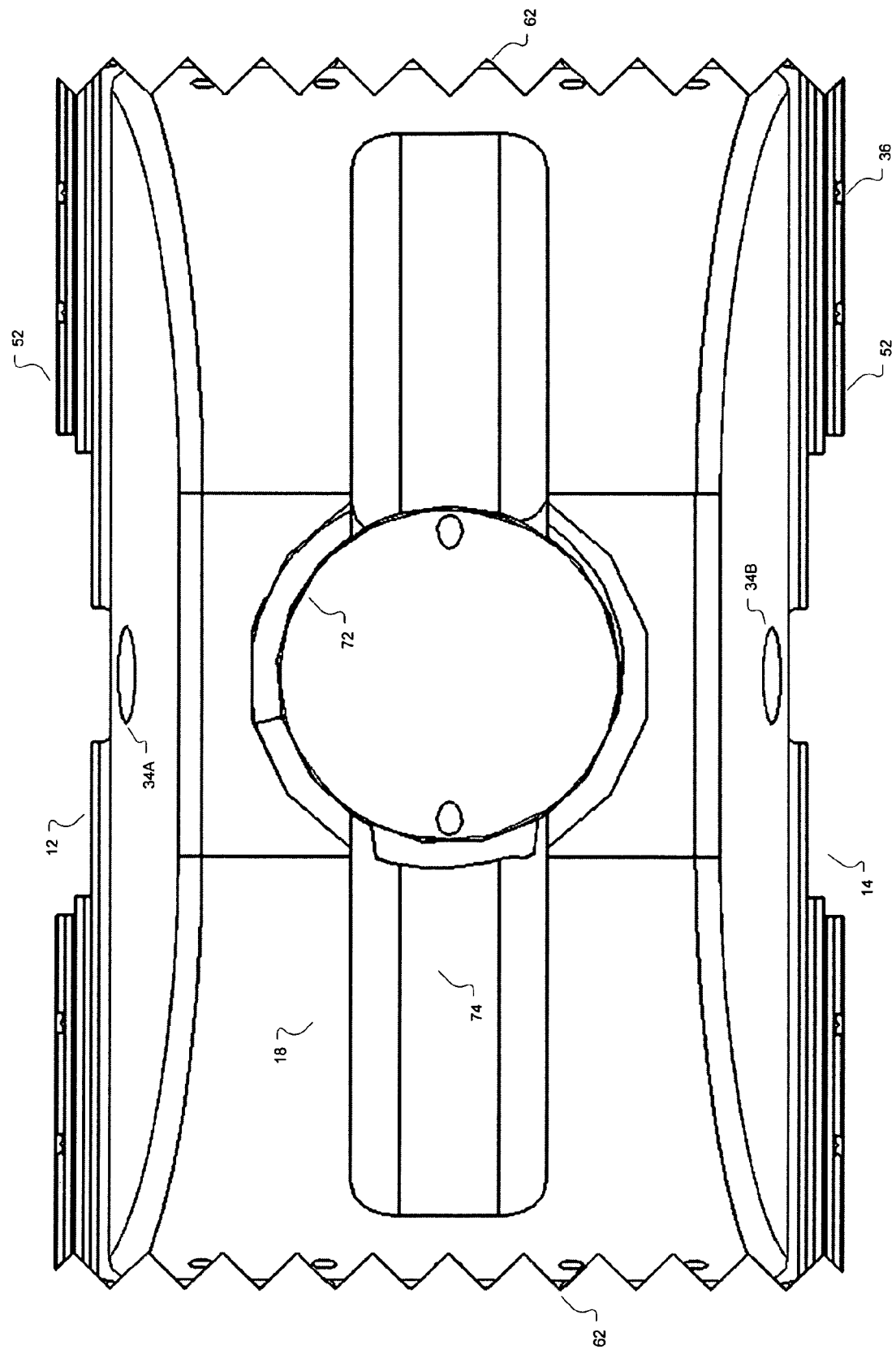

FIG. 2F is a simplified, partial view of the mammalian bony segment stabilization implant 10 top 12 and bottom 14 teeth 52 according to various embodiments. The teeth 52 has a forward surface 53 and back surface 54 where the surfaces form a reverse rack relative the implant 10 front 16 to limit or prevent implant movement toward the rear surface 18 after implantation between bony segments 222 to be stabilized. FIG. 2G is a simplified, top 12 view of the mammalian bony segment stabilization implant 10 according to various embodiments. As shown in FIG. 2G the implant 10 includes a large central fenestration 37, radio opaque marker fenestrations 32, 34A, and plurality of partial, surface fenestrations or openings 36.

FIG. 2H is a simplified, front view 16 of the mammalian bony segment stabilization implant 10 according to various embodiments. As shown in FIG. 2H, the implant 10 front 16 includes sloped ends or surfaces 15 that may a user to distract a bony segment pair 222 when the implant 10 is inserted between the pair. FIG. 2I is a simplified, rear 18 view of the mammalian bony segment stabilization implant 10 according to various embodiments. As shown in FIG. 2I the implant 10 rear section 18 may include a tool recess 74 including a threaded section 72 to enable a user to releasably engage the implant 10 for insertion or removal between a bony segment 222 pair.

Figure 2J:
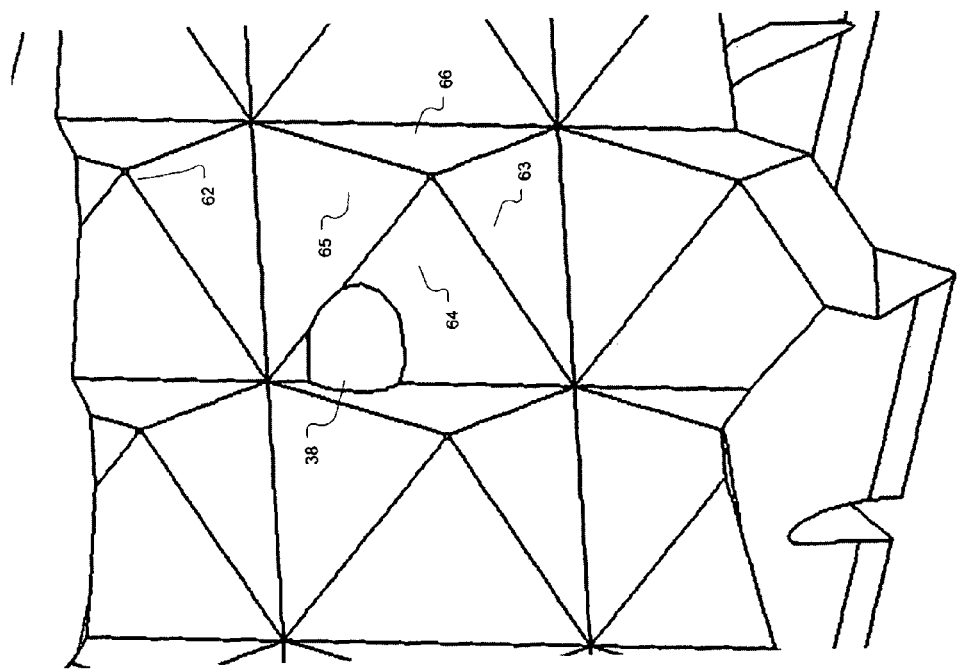
FIG. 2J is a simplified, partial view of a mammalian bony segment stabilization implant side protrusions according to various embodiments.
Figure 2K:
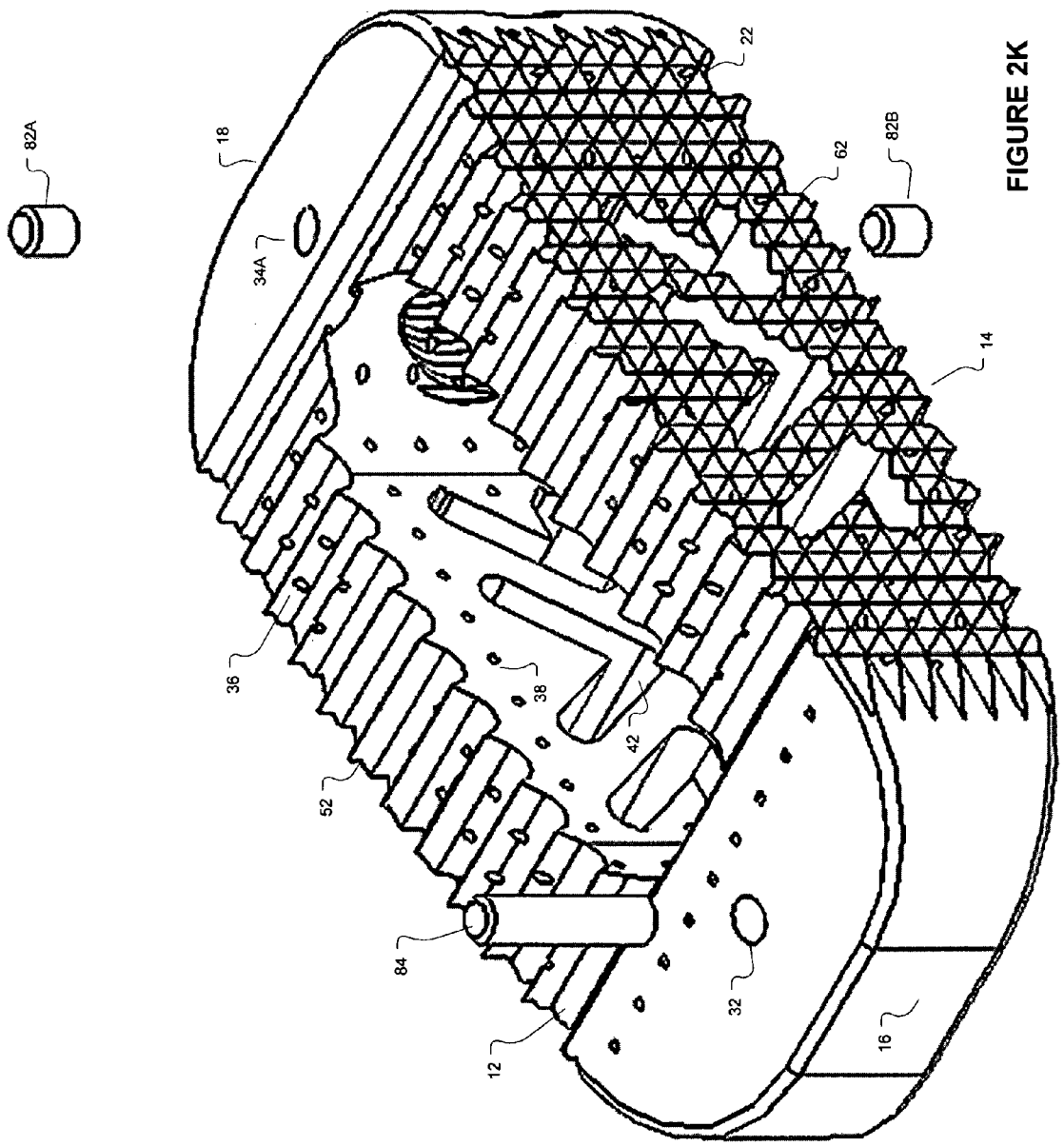
FIG. 2K is a simplified, isometric front view of a mammalian bony segment stabilization implant including radio opaque elements according to various embodiments.

FIG. 2J is a simplified, partial view of the mammalian bony segment stabilization implant 10 side 22, 24 protrusions 62 according to various embodiments. As shown in FIG. 2J the side protrusions 62 may form a diamond knurl pattern where each protrusion 62 has a four-sided 63, 64, 65, 66 pyramid shape. As also shown side fenestrations 38 may be formed in some protrusions 62 where the fenestrations 38 may enable bony in-growth. FIG. 2K is a simplified, isometric front view of the mammalian bony segment stabilization implant 10 including radio opaque elements or markers 82A, 82B, 84 according to various embodiments. The radio opaque elements or markers 82A, 82B, 84 may be inserted into implant 10 fenestrations 34A, 34B, and 32, respectively to enable a user to determine implant 10 placement between bony segments 222 via a radio wave generation device. It is noted that the implant 10 may be comprised of any biocompatible material including bone, polymers, and metals.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. A method for stabilizing a bony segment pair, comprising inserting a horizontally elongate element between the bony segment pair, the horizontally elongate element having a long horizontal axis, a front, a top surface, a first side surface, a second side surface, a bottom surface, and a rear, the element having a length from the front to the rear and a width from the first side to the second side, the elongate element defining:

a central opening extending from the top to the bottom, the central opening having a length and a width, the central opening length greater than half the element length and the central opening width greater than one-third the element width;

a plurality of partial depth surface openings each of a 0.25 mm diameter on the top surface; and a plurality of partial depth surface openings each of a 0.25 mm diameter on the bottom surface;

a plurality of partial and full depth surface openings each of a 0.25 mm diameter on the first side surface;
a plurality of partial and full depth surface openings each of a 0.25 mm diameter on the second side surface; and
each of the plurality of the partial depth surface openings having a length less than one-tenth the central opening length and a width less than one-fifth the central opening width, and wherein each partial depth surface opening does not penetrate entirely therethrough to their respective opposite surface and the full depth surface openings on each first or second side does penetrate entirely therethrough to their respective opposite surface extending to the central opening, each partial or full depth surface opening is spaced 1.25 mm vertically and horizontally from each adjacent surface opening and wherein one of a bone growth activator and a bio-active element is embedded in each of the plurality of the partial and full depth surface openings.

2. The method of claim 1, wherein the elongate element top is arcuate and bottom is arcuate.

3. The method of claim 1, wherein the top surface and the bottom surface comprises a plurality of teeth oriented transverse to the long axis and inclined to the element rear.

4. The method of claim 3, wherein the distance between adjacent teeth is at least twice the height of the teeth.

5. The method of claim 4, wherein the bony segment pair is a first vertebra adjacent to a second vertebra.

6. The method of claim 1, wherein the first side and the second side comprises a plurality of protrusions extending transverse to the long axis.

7. The method of claim 6, wherein each of the plurality of protrusions extending traverse to the long axis comprises four sides forming a pyramid.

8. The method of claim 1, wherein the elongate element defines a plurality of fenestrations extending from the first side to the second side via the central opening.

9. A horizontally elongate element for stabilizing a bony segment pair, the horizontally elongate element comprising:
  a long horizontal axis;
  a front
  a top surface defining, a plurality of partial depth surface openings each of a 0.25 mm diameter;
  a first side surface defining, a plurality of partial and full depth surface openings each of a 0.25 mm diameter;
  a second side surface defining, a plurality of partial and full depth surface openings each of a 0.25 mm diameter;
  a bottom surface defining, a plurality of partial depth surface openings each of a 0.25 mm diameter;
  a rear; and
  defining a central opening extending from the top to the bottom, the central opening having a length and a width, the central opening length greater than half the element length and the central opening width greater than one-third the element width and each of the plurality of the partial depth surface openings having a length less than one-tenth the central opening length and a width less than one-fifth the central opening width, and wherein the partial depth surface openings do not penetrate entirely therethrough their respective opposite surface and the full depth surface openings on each first or second side does penetrate entirely therethrough to their respective opposite surface extending to the central opening, each partial or full depth surface opening is spaced 1.25 mm vertically and horizontally from each adjacent surface opening and wherein one of a bone growth activator and a bio-active element is embedded in each of the plurality of the partial and full depth surface openings.

10. The element of claim 9, wherein the elongate element top is arcuate and bottom is arcuate.

11. The element of claim 9, wherein the top surface and the bottom surface comprises a plurality of teeth oriented transverse to the long axis and inclined to the element rear.

12. The method of claim 11, wherein the distance between adjacent teeth is at least twice the height of the teeth.

13. The element of claim 12, wherein the bony segment pair is a first vertebra adjacent to a second vertebra.

14. The element of claim 9, wherein the first side and the second side comprises a plurality of protrusions extending transverse to the long axis.

15. The element of claim 14, wherein each of the plurality of protrusions extending traverse to the long axis including four sides forming a pyramid.

16. The element of claim 9, wherein the elongate element defines a plurality of fenestrations extending from the first side to the second side via the central fenestration.

* * * * *